(12) United States Patent
Pond, Jr. et al.

(10) Patent No.: US 7,993,344 B2
(45) Date of Patent: Aug. 9, 2011

(54) GUIDE AND METHOD FOR INSERTING AN ELONGATED MEMBER INTO A PATIENT

(75) Inventors: John Durward Pond, Jr., Germantown, TN (US); Jonathan M. Dewey, Memphis, TN (US); Christopher M. Patterson, Olive Branch, MS (US); Thomas A. Carls, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1170 days.

(21) Appl. No.: 11/691,178

(22) Filed: Mar. 26, 2007

(65) Prior Publication Data

US 2008/0243052 A1    Oct. 2, 2008

(51) Int. Cl.
*A61B 17/70*    (2006.01)
(52) U.S. Cl. ........................................ 606/86 A
(58) Field of Classification Search .......... 606/86 A, 606/86 R, 246, 104, 105, 90, 99, 146
See application file for complete search history.

(56) References Cited

U.S. PATENT DOCUMENTS

| | | | |
|---|---|---|---|
| 5,571,109 A * | 11/1996 | Bertagnoli | 606/86 A |
| 6,530,929 B1 | 3/2003 | Justis et al. | |
| 2002/0161368 A1* | 10/2002 | Foley et al. | 606/61 |
| 2005/0171540 A1 | 8/2005 | Lim et al. | |
| 2006/0111728 A1* | 5/2006 | Abdou | 606/86 |
| 2008/0221586 A1* | 9/2008 | Garcia-Bengochea et al. | 606/108 |

* cited by examiner

*Primary Examiner* — Eduardo C Robert
*Assistant Examiner* — Summer L Kostelnik

(57) ABSTRACT

The present application is directed to guides for inserting an elongated member into a patient. The guide generally includes an elongated shape with a distal end that is positioned within the patient, and a proximal end that may be positioned outside of the patient. The guide may include a channel formed between sidewalls. The channel is sized to receive the elongated member and guide the member into a predetermined location within the patient. In one embodiment, the guide is used with an insertion device that may include a pivoting carriage for initially inserting the guide and then the elongated member into the patient. The guide may also be used in a freehand technique that is positioned specifically within the patient by the surgeon.

12 Claims, 13 Drawing Sheets

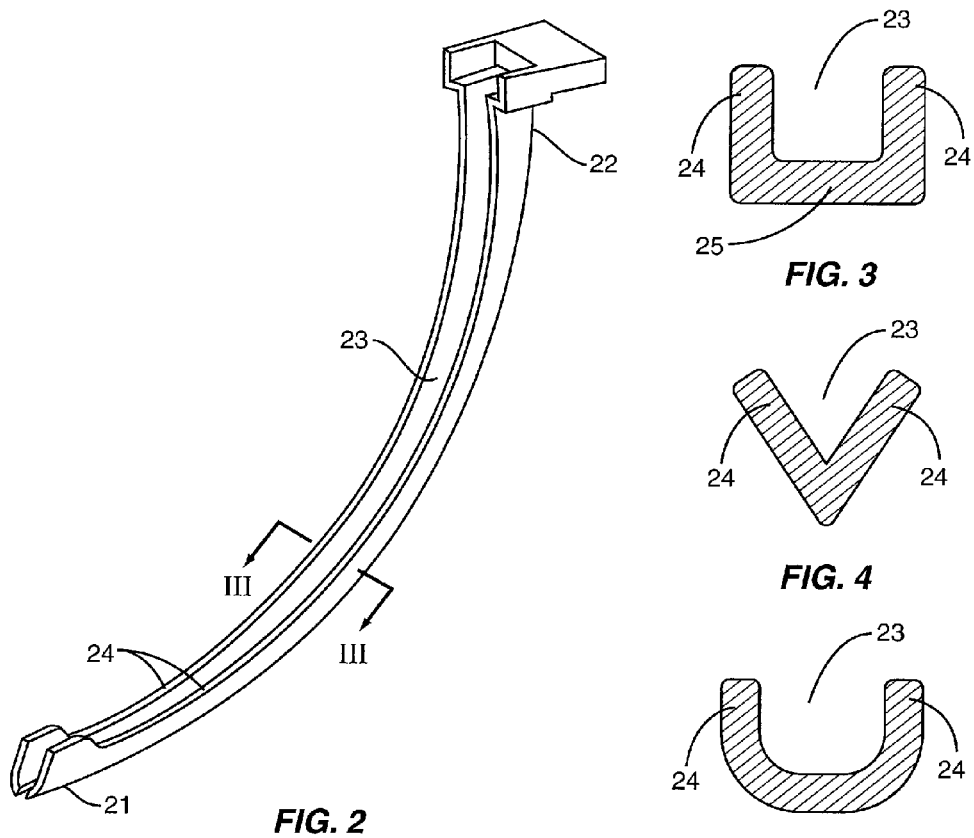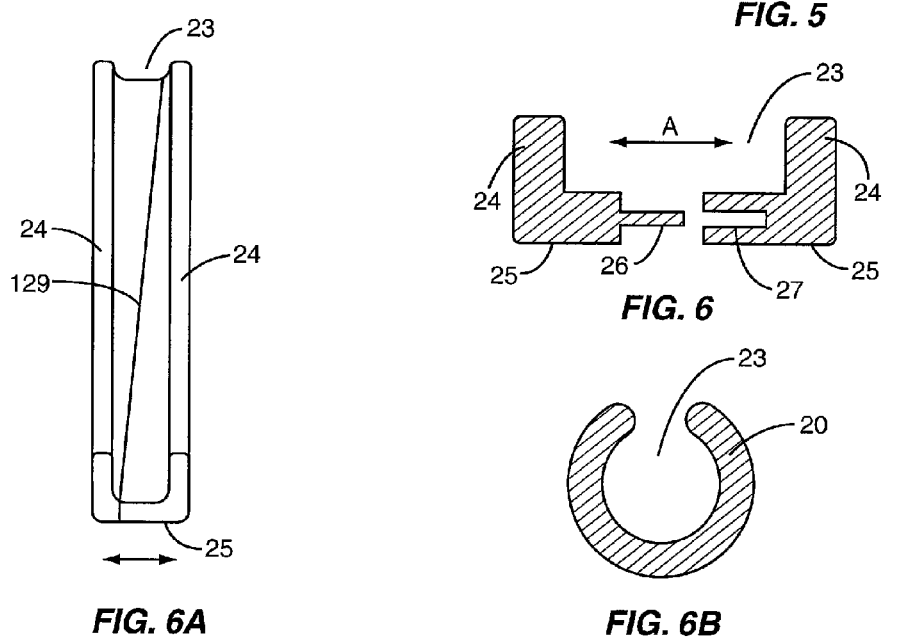

GUIDE AND METHOD FOR INSERTING AN ELONGATED MEMBER INTO A PATIENT

BACKGROUND

The application is a guide for insertion of an elongated member into a patient and, more particularly, to a guide with a channel to receive and position the elongated member percutaneously within a patient.

Elongated members such as rods, cables, wires, and the like are inserted into patients during various surgical procedures. One example is a vertebral rod implanted to support and position two or more vertebral members in one or more regions of the spine. The elongated member is attached by anchors to the vertebral members when positioned within the patient.

Often times the elongated members are constructed of a material that bends or flexes upon the application of an insertion force. This property often makes it difficult to insert the elongated member into the patient as the leading tip moves off course during insertion. Previous insertion methods have required a large incision through the skin and detachment of muscles to access the implant site. This type of procedure usually results in a longer surgical procedure with greater amounts of blood loss and increased anesthesia time. These procedures may also have a higher risk of infection, require a longer postoperative recovery time, and result in additional pain and discomfort to the patient.

It is also necessary for accurate placement of the elongated member within the patient. A guide should provide a route for accurately inserting the elongated member. The guide should also be sized for a minimum incision to reduce the damage to the patient.

SUMMARY

The present application is directed to guides for inserting an elongated member into a patient. The guide generally includes an elongated shape with a distal end that is positioned within the patient, and a proximal end that may be positioned outside of the patient. The guide may include a channel formed between sidewalls. The channel may be sized to receive the elongated member and guide the member into a predetermined location within the patient. In one embodiment, the guide is used with an insertion device that may include a pivoting carriage for initially inserting the guide and then the elongated member into the patient. The guide may also be used in a freehand technique that is positioned independently into the patient by the surgeon.

BRIEF DESCRIPTION OF THE DRAWINGS

FIG. 2 is a perspective view of a guide according to one embodiment.

FIG. 3 is a sectional view taken along line III-III of FIG. 2 illustrating a shape of a channel.

FIG. 4 is a section view illustrating a shape of a channel according to one embodiment.

FIG. 5 is a section view illustrating a shape of a channel according to one embodiment.

FIG. 6 is an exploded sectional view of guide constructed of first and second sections according to one embodiment.

FIG. 6A is a perspective view of guide constructed of first and second sections according to one embodiment.

FIG. 6B is a sectional view illustrating a guide constructed according to one embodiment.

DETAILED DESCRIPTION

The present application is directed to a device for guiding an elongated member into a patient. The device may be constructed for percutaneous use with a distal section being inserted into the patient and a proximal section remaining outside of the patient. Once the device is inserted, it forms a guide for inserting and positioning the elongated member within the patient.

Figure 1:
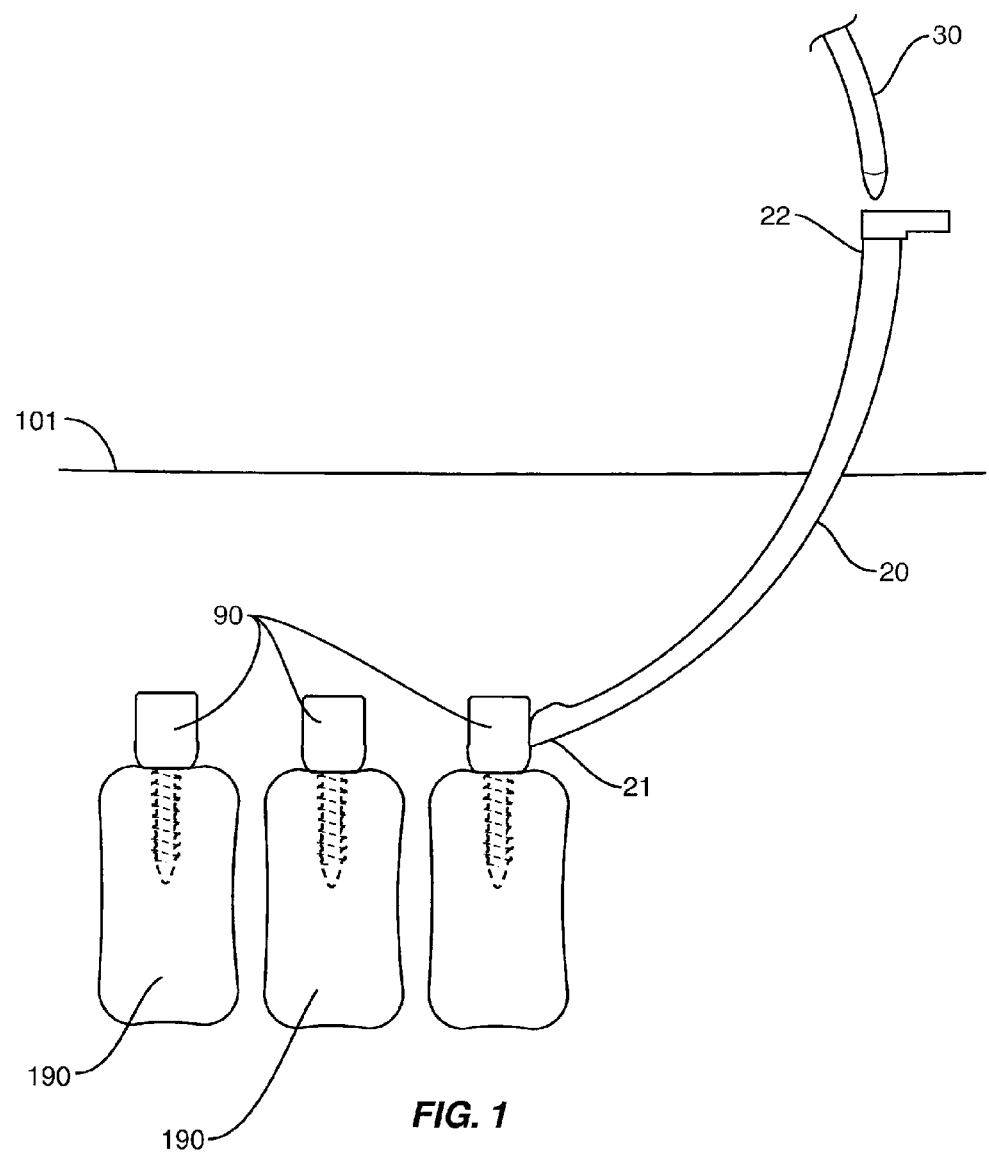
FIG. 1 is a schematic diagram of a slide inserted within a patient according to one embodiment.

FIG. 1 illustrates a schematic view of one embodiment of a device 20, generally referred to as a guide. Guide 20 includes an elongated shape with a distal end 21 and a proximal end 22. Guide 20 is inserted into the patient with the distal end 21 inserted through the skin 101 and into the patient while the proximal end 22 remains exterior to the patient. Guide 20 forms an insertion route for positioning an elongated member 30 into the patient. In this embodiment, guide 20 directs the elongated member 30 to anchors 90 for attachment to bony members 190.

Guide 20 acts as a conduit for placement of the elongated member 30 into the patient. The elongated member 30 may be constructed of a material that may be unable to be inserted directly into the patient without adverse flexing that makes positioning difficult, or may even cause damage to the member. FIG. 2 illustrates one embodiment of the guide 20 with an elongated shape that terminates at a distal end 21 and a proximal end 22. A channel 23 is sized to receive the elongated member 30. Channel 23 may extend the entire length of the guide 20 with open distal and proximal ends as illustrated in the embodiment of FIG. 2, or along a limited length. Channel 23 may include a variety of different shapes. FIG. 3 includes one embodiment with the channel 23 formed by opposing sidewalls 24 and an intermediate side 25. In this embodiment, sidewalls 24 are substantially parallel. FIG. 4 illustrates another embodiment that is substantially V-shaped with a pair of sidewalls 24. FIG. 5 illustrates an embodiment with a continuous sidewall 24 with a curved configuration that forms the channel 23.

In some embodiments, channel 23 includes a fixed shape and size. In other embodiments, channel 23 is adjustable depending upon the context of use. FIG. 6 includes a guide 20 constructed as two separate sections. A first section includes a sidewall 24 and a tab 26 that extends outward from an intermediate side 25. A second section includes a corresponding sidewall 24 and intermediate side 25 with a receptacle 27 sized to receive the tab 26. The first and second sections are adjustable in directions indicated by arrow A. Adjustment of the sections provides for varying the size of the channel 23 to receive a variety of sizes of elongated members 30. In another embodiment, guide 20 is constructed of a flexible material that allows the size of the channel 23 to vary depending upon the size of the elongated member 30. FIG. 6A illustrates another embodiment with first and second sections connected together along diagonal surfaces 129. The size of the channel 23 may be adjusted by sliding the surfaces 129 across each other. In another embodiment as illustrated in FIG. 6B, guide 20 is made of a flexible material that is biased towards a first shape with a closed or reduced channel 23. Guide 20 is flexible such that insertion of the elongated member 30 causes the guide 20 to generally conform to the shape of the elongated member 30.

Figure 7:
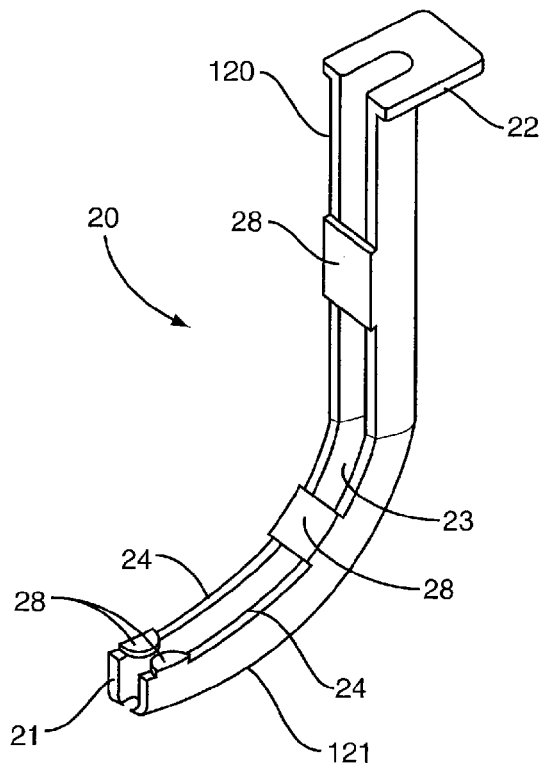
FIG. 7 is a perspective view of a guide according to one embodiment.

Guide 20 may include a substantially open side that leads into the channel 23 as illustrated in FIG. 2. In other embodiments, channel 23 is covered along one or more sections. FIG. 7 includes extensions 28 that extend from the sidewalls 24 over the channel 23. Extensions 28 may extend completely across the channel 23 such as the two proximal extensions 28 of FIG. 7. Alternatively, extensions 28 may extend a limited distance from one or both sidewalls 24 leaving an opening over the channel 23 as illustrated by the distal extension 28 of FIG. 7.

The overall shape of the guide 20 may vary depending upon the context of use. In one embodiment as illustrated in FIG. 2, guide 20 is curved substantially along the entire length. In another embodiment as illustrated in FIG. 7, guide 20 includes a first section 120 that is substantially straight, and a second curved section 121. In this embodiment, the first straight section 120 is at the proximal portion of the guide 20 and the curved section 121 at the distal portion. In another embodiment, the distal section is substantially straight and the proximal section curved. Further, guide 20 may include multiple curved and straight sections along the length.

Figure 8:
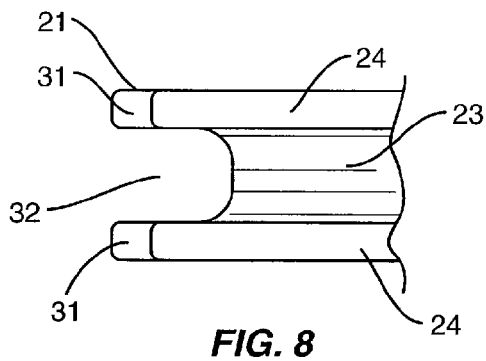
FIG. 8 is a partial top view of a distal section of a guide according to one embodiment.
Figure 9:
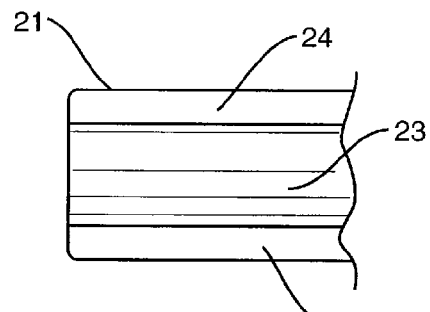
FIG. 9 is a partial top view of a distal section of a guide according to one embodiment.

The distal end 21 is positioned within the patient to deliver the elongated member 30. FIG. 8 illustrates one embodiment that includes a pair of opposing fingers 31 separated by an opening 32. The opening 32 is sized for insertion of a set screw as will be explained in detail below. In this embodiment, the fingers 31 are aligned with and extend outward from the sidewalls 24. FIG. 9 illustrates another embodiment with the sidewalls 24 extending completely to the distal end 21.

Figure 10:
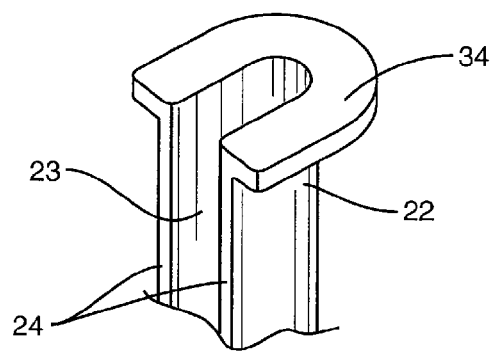
FIG. 10 is a partial perspective view of a proximal section of a guide according to one embodiment.

As illustrated in FIG. 10, the proximal end 22 may include a flange 34. Flange 34 is positioned at the end of the channel 23 and may include a larger width than the sidewalls 24. Flange 34 provides a handle for grasping and manipulating the guide 20 during the surgical procedure. Flange 34 may also act as a stop to limit the extent of insertion of the guide 20 into the patient.

Figure 11:
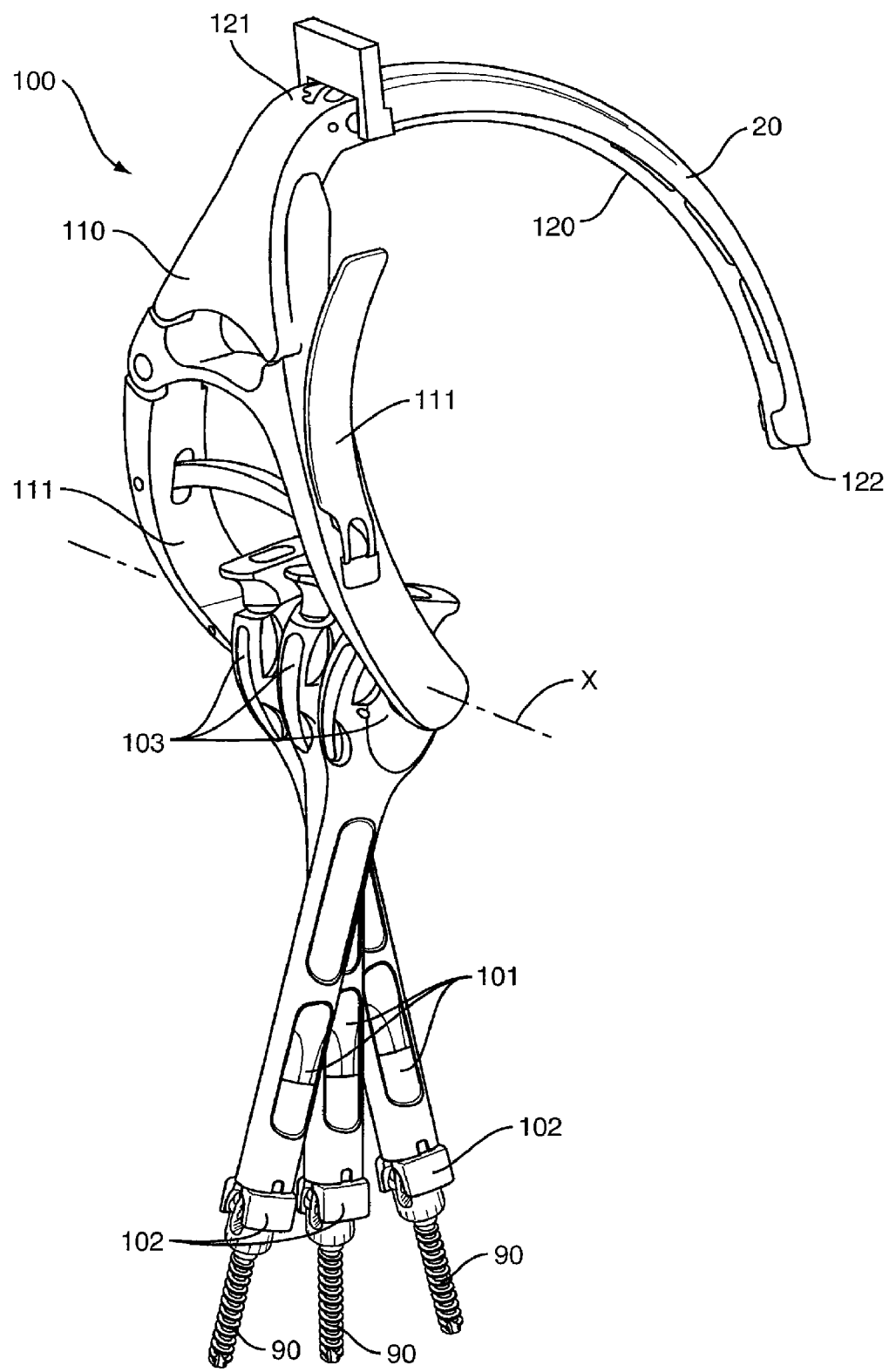
FIG. 11 is a perspective view of a guide mounted on an inserter in a first orientation prior to insertion into a patient according to one embodiment.
Figure 12:
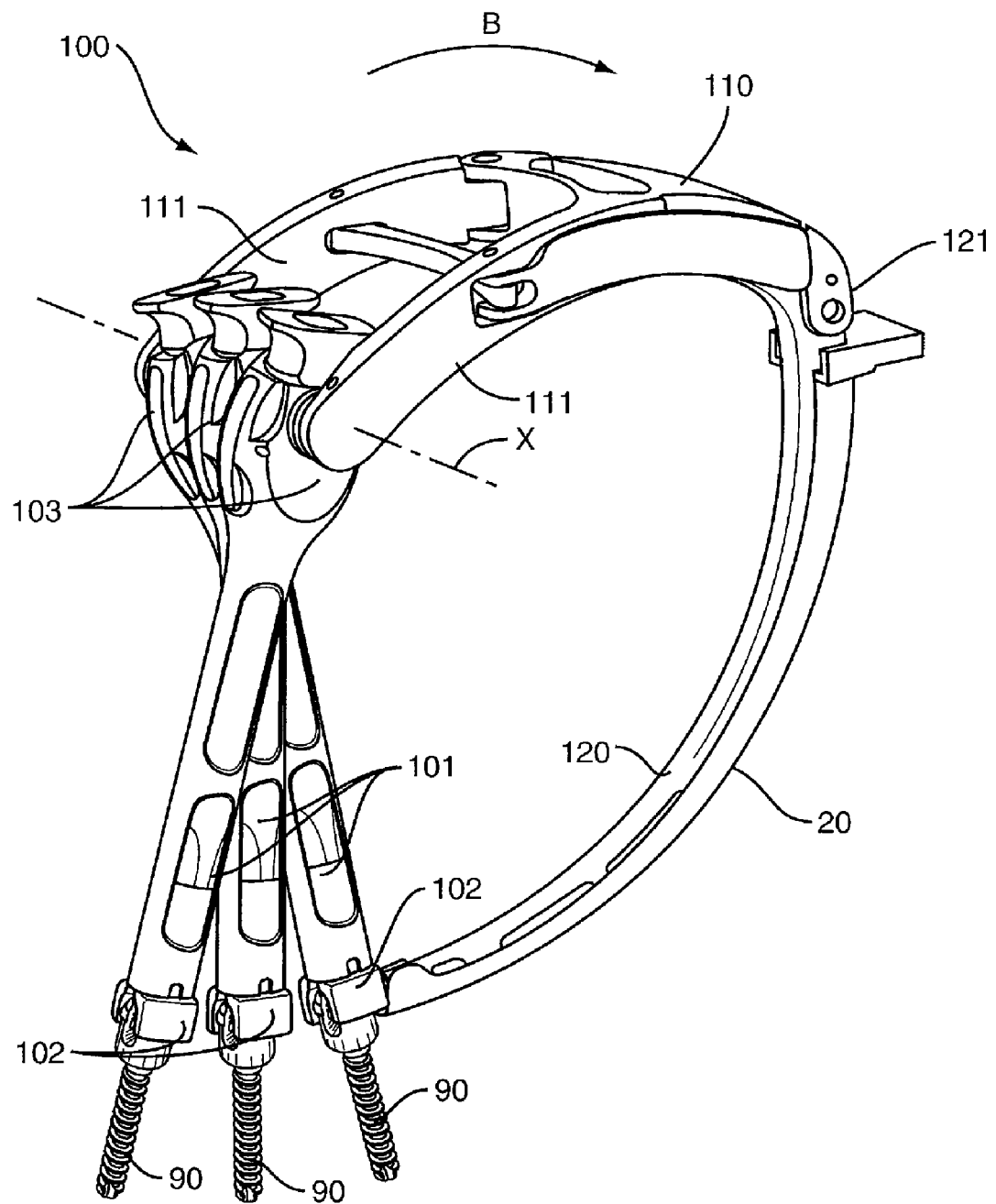
FIG. 12 is perspective view of a guide mounted on an inserter in a second orientation inserted into a patient according to one embodiment.

The guide 20 may be used in many different applications. One application of the guide 20 is with a SEXTANT rod insertion system available from Medtronic Sofamor Danek of Memphis, Tenn. FIG. 11 illustrates the guide 20 mounted to the rod insertion system 100. The rod insertion system 100 includes a carriage 110 that is pivotally mounted to one or more extensions 101. Carriage 110 includes an elongated inserter 120 that is inserted into the patient. Carriage 110 moves about a pivot axis X between a first orientation as illustrated in FIG. 11 with the inserter 120 away from the patient, and a second orientation as illustrated in FIG. 12 with the inserter 120 positioned within the patient. Guide 20 is sized to mount to the inserter 120 for insertion and positioning into the patient. Embodiments of insertion systems are disclosed in U.S. Pat. No. 6,530,929 and U.S. Patent Application Publication 2005/0171540 each incorporated herein by reference.

Extensions 101 are hollow conduits that are attached to the anchors 90 mounted to the bony members within the patient. Extensions 101 include a distal end 102 that attaches to the anchors 90 and a proximal end 103 operatively connected to the carriage 110. In one embodiment, a shaft (not illustrated) extends through each extension 101 along the pivot axis X to connect the carriage 110 to the extensions 101.

Extensions 101 include a hollow interior for receiving a set screw to attach the elongated member 30 to the anchor 90. Extensions 101 may include an elongated shape such that the proximal end 103 remains exterior to the patient during the surgical procedure. In multiple-extension embodiments, each of the extensions 101 may be substantially identical or may be different.

Extensions 101 may attach to a variety of different anchors 90. Examples of the anchors 90 include but are not limited to top-loading, side loading, off-set connectors, cross-link connectors, fixed angle screws, and multi-angle screws.

Carriage 110 is pivotally attached to the extensions 101 and movable between the first and second orientations. Carriage 110 includes a first end with opposing arms 111 that are spaced apart and straddle the extensions 101. The inserter 120 is positioned at the ends of the arms 111 and includes an elongated shape that extends from a first end 121 at the arms 111 and terminates at a distal tip 122. The tip 122 and/or distal end 21 of the guide 20 may be sharpened to facilitate insertion of the inserter 120 into the patient. The sectional shape of the inserter 120 may be the same as the channel 23. In one embodiment, inserter 120 is substantially rectangular to correspond to the channel 23 of FIG. 3. Other embodiments may include a triangular shape that corresponds to the guide 20 of FIG. 4, and a circular shape of the guide 20 of FIG. 5.

The guide 20 may attach to the inserter 120 in various manners. In one embodiment, the inserter 120 includes a tapered width that increases from the distal tip 122 towards the first end 121. Attachment includes aligning the proximal end 22 of the guide 20 with the distal tip 122 of the inserter 120. The guide 20 is then slid in a proximal direction with the inserter 120 within the channel 23. Sliding may continue until the increasing width of the inserter 120 matches the width of the channel 23. In one embodiment, further proximal movement of the guide 20 coincides with the distal end 21 of the guide 20 substantially aligned with the distal tip 122 of the inserter 120. In another embodiment, the channel 23 includes a tapered width that controls the positioning of the guide 20 on the inserter 120. In another embodiment, both inserter 120 and channel 23 are tapered.

Another attachment method includes aligning the guide 20 along the inserter 120. Once aligned, the guide 20 is laterally moved to capture the inserter 120 within the channel 23. In one embodiment, the guide 20 flexes outward during insertion of the inserter 120 thus creating a biasing force that locks the guide 20 onto the exterior of the inserter 120.

Figure 14:
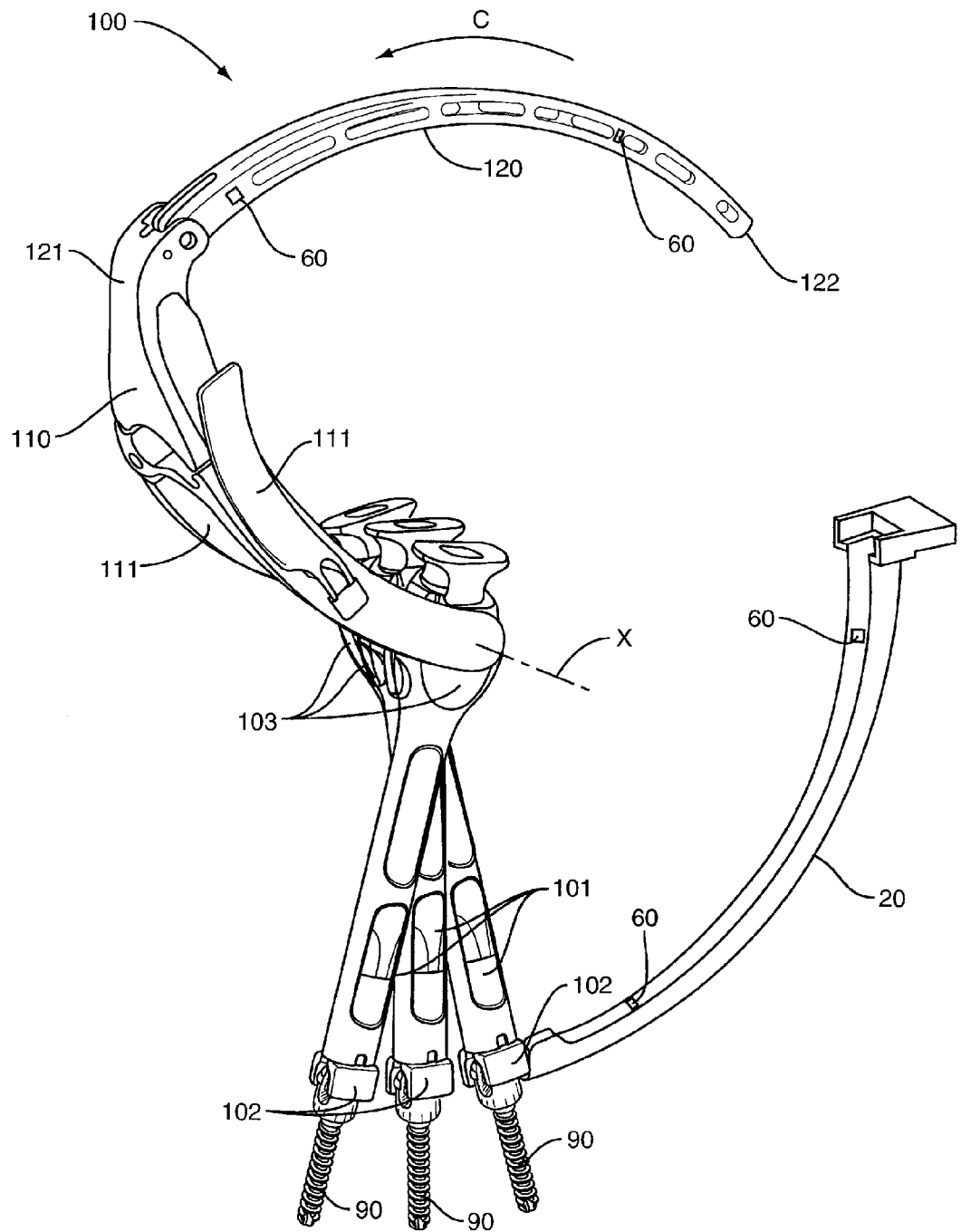
FIG. 14 is a perspective view of a guide within a patient and the inserter in a first orientation according to one embodiment.

One or both of the inserter 120 and the guide 20 may include a locking mechanism 60 to attach the guide 20 to the inserter 120. FIG. 14 illustrates one embodiment with a pair of locking mechanisms 60 on each of the guide 20 and inserter 120. Locking mechanisms 60 may include various embodiments including a ball and detent combination, a biased member that extends outward from and contacts a receiving surface, slot and groove arrangement, ramped features, ratchet teeth, over-center latching mechanism, Nitinol and shape-memory latches, and threaded pins. In one embodiment, locking mechanism 60 includes a rim at the proximal end 22 of the guide 20 that attaches within a notch at the first end 121 of the inserter 120.

One embodiment of using the guide 20 with the rod insertion system 100 is illustrated in FIGS. 11-17. Prior to use of the guide 20, the system 100 is mounted with the extensions 101 attached to anchors 90 positioned within the patient. In one embodiment, the proximal end 103 and carriage 110 are exterior to the patient with the distal ends 102 of the extensions 101 within the patient. For purposes of clarity, the patient is not illustrated in FIGS. 11-17. The guide 20 is attached to the inserter 120 when it is in a first orientation as illustrated in FIG. 11. As previously explained, the guide 20 may be slid or snap-fit onto the inserter 120. In one embodiment, the guide 20 and inserter 120 include substantially the same radius of curvature. In another embodiment, the guide 20 includes a different radius of curvature.

After attachment, the carriage 110 is pivoted about the pivot axis X relative to the extensions 101 to move the carriage to a second orientation with the inserter 120 and guide 20 within the patient. As illustrated in FIG. 12, the pivoting movement is in the direction of arrow B. The distal section 21 of the guide 20 and distal tip 122 of the inserter 120 include a relatively small area which facilitates insertion into the patient. In one embodiment, the distal end of section 21 may be sharpened to further facilitate the insertion. The carriage 110 continues to be pivoted until the distal section 21 is positioned relative to the first extension 101. In one embodiment as illustrated in FIG. 12, this includes the distal section 21 contacting the outer side of the extension 101. This may include the fingers 31 (FIG. 8) inserted into the distal end 102 of the first extension 101 with the opening 32 positioned over the anchor 90. In another embodiment, the distal section 21 is in proximity to but spaced away from the outer side of the extension 101. In another embodiment, the guide 20 is positioned within one or more of the extensions 101.

Figure 13:
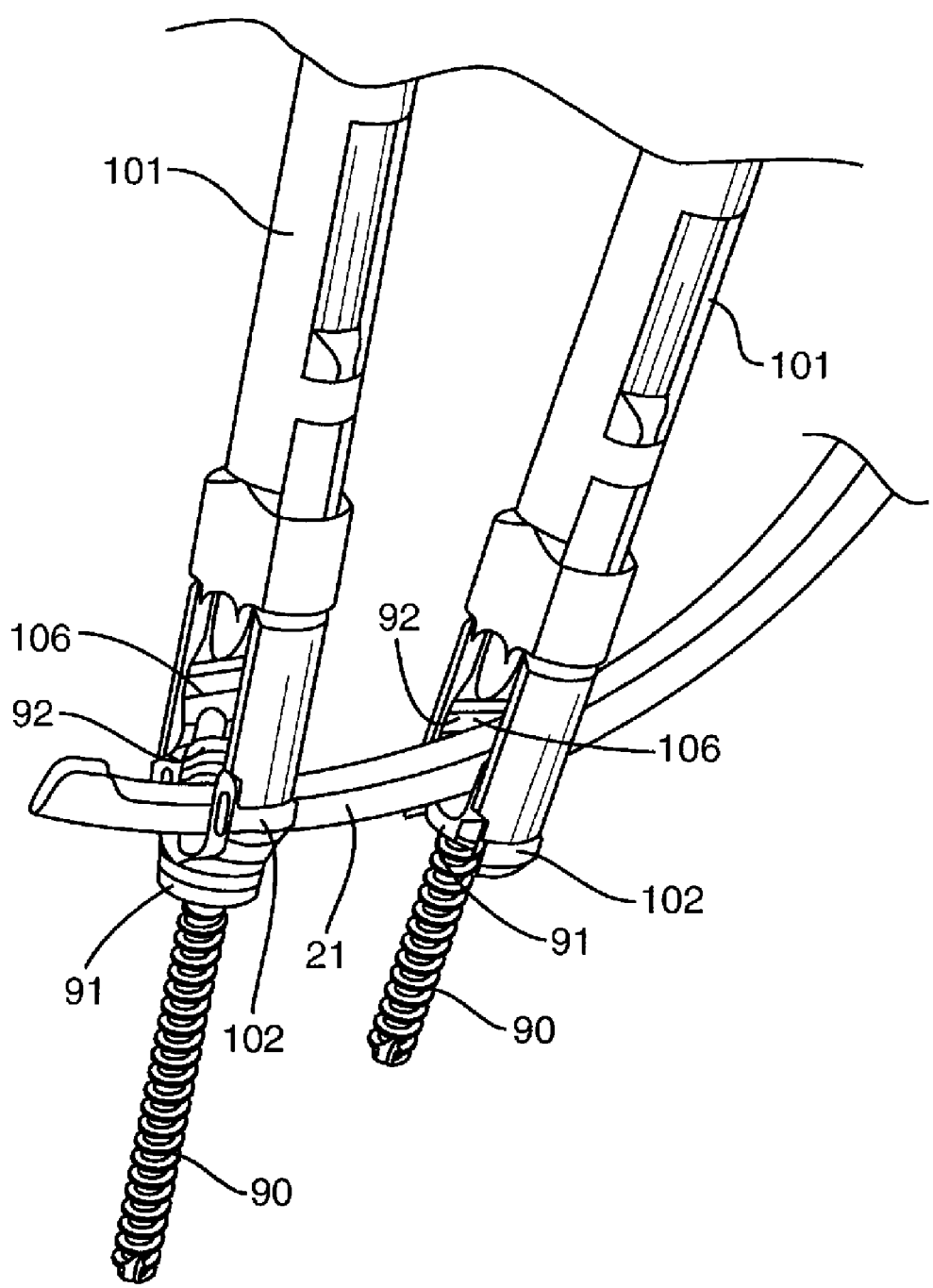
FIG. 13 is a partial perspective view of a guide inserted within extensions according to one embodiment.

FIG. 13 includes an embodiment with anchors 90 including a saddle 91 with an opening 92. Extensions 101 also include an opening 106 at the distal end 102. Extensions 101 are mounted with the openings 106 aligned with the opening 92 in the saddle 91. The combined openings 92, 106 are sized to initially receive the guide 20 and subsequently the elongated member 30. In one embodiment, the guide 20 extends outward from the distal tip 122 of the inserter 120 and only the guide is positioned within the extensions 101. In another embodiment, both the guide 20 and inserter 120 are positioned within the extensions.

Figure 15:
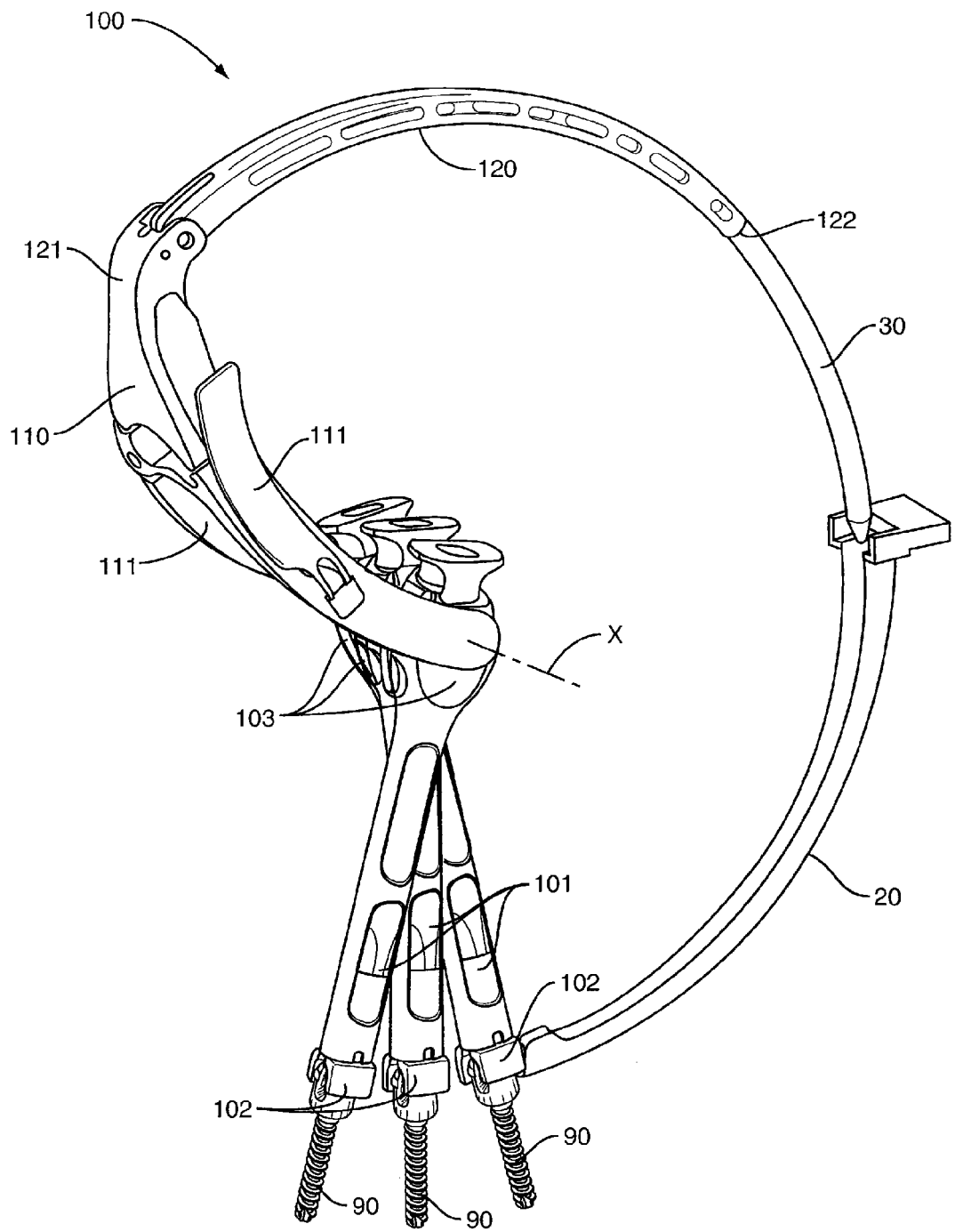
FIG. 15 is a perspective view of a guide within a patient and an elongated member being moved into the guide by an inserter according to one embodiment.

Returning to the overall method, FIG. 14 illustrates the next step with the inserter 120 moved back to the first orientation once the guide 20 is positioned within the patient. Specifically, the carriage 110 is pivoted about the pivot axis X in the direction of arrow C thus removing the inserter 120 from the patient. During removal, the inserter 120 moves within the channel 23 thus allowing the guide 20 to remain positioned within the patient. As illustrated in FIG. 15, the elongated member 30 is then mounted to the inserter 120. The elongated member 30 may extend outward from the distal tip 122 of the inserter 120, or may be positioned inward from the tip 122. Inserter 120 may be hollow and sized to contain the member 30.

Figure 16:
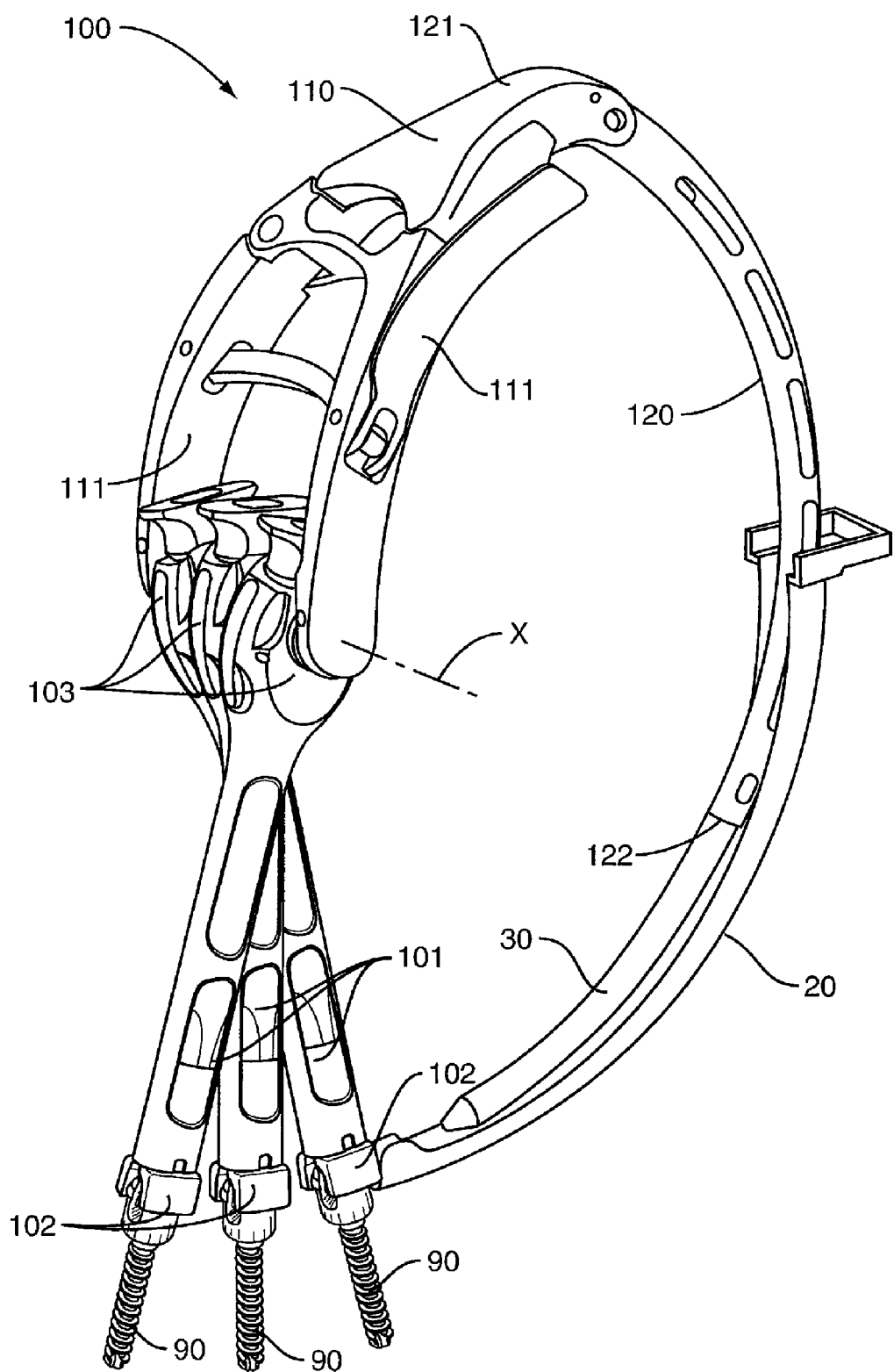
FIG. 16 is a perspective view of a guide within a patient and an elongated member being moved through the guide by an inserter according to one embodiment.

Once the elongated member 30 is mounted to the inserter 120, the carriage 110 is again pivoted about the pivot axis X and the inserter 120 and elongated member 30 are moved from the first orientation towards the second orientation and into the patient. As illustrated in FIG. 16, this movement causes the elongated member 30 to move along the channel 23. Guide 20 protects the member 30 during the insertion into the patient and directs the leading end to the extensions 101. The elongated member 30 may contact and slide along the sides 24, 25 of the channel 23 during the insertion. This contact limits any flexing of member 30 which may possibly cause damage to or deflection of the member 30.

Figure 17:
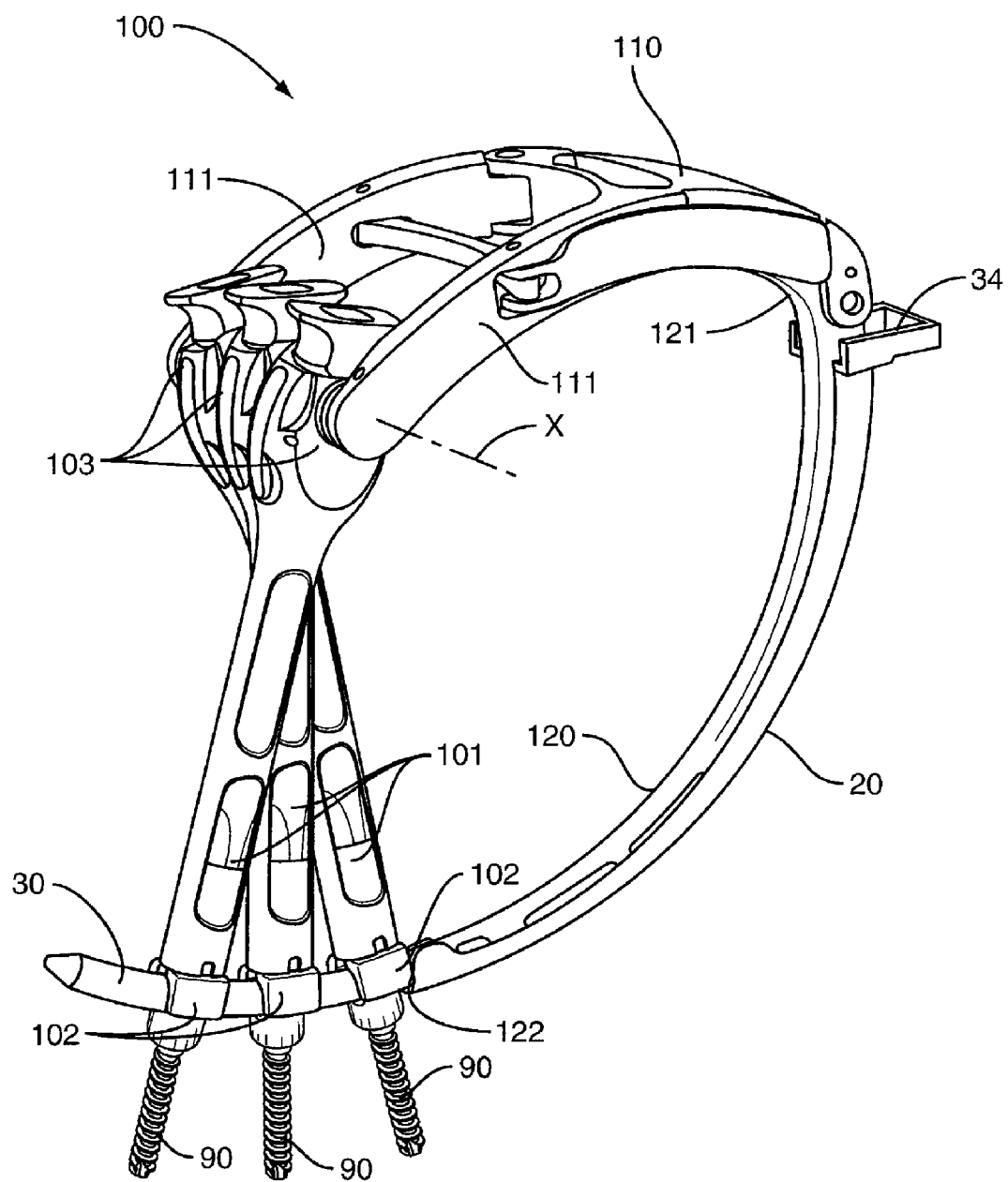
FIG. 17 is a perspective view of a guide within a patient and an elongated member positioned within extensions according to one embodiment.

FIG. 17 illustrates the carriage 110 moved to the second orientation and the elongated member 30 being inserted into each of the extensions 101. Once in this position, set screws (not illustrated) may be inserted through the hollow interiors of the extensions 101 to permanently attach the elongated member 20 to each anchor 90. The inserter 120 and guide 20 may then be removed from the patient. In one embodiment, the guide 20 remains attached to the inserter 120 and is removed as the carriage 110 moves back to the first orientation. In another embodiment, the guide 20 is detached from the inserter 120 and the two elements are separately removed from the patient. Flange 34 provides a convenient handle for grasping and removing the guide 20 from the patient.

Figure 18:
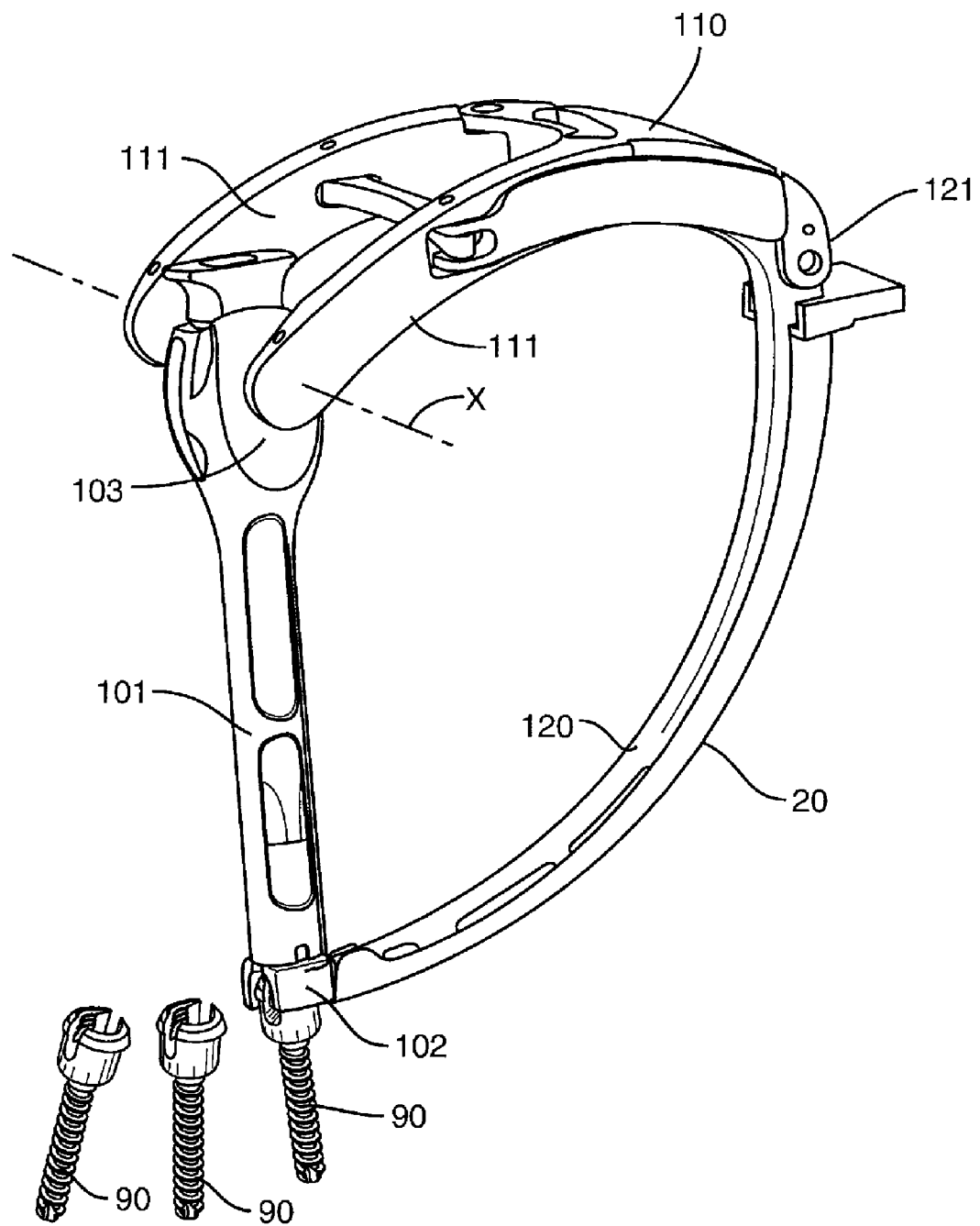
FIG. 18 is a perspective view of a guide mounted on an inserter in a second orientation inserted into a patient according to one embodiment.

The embodiment described in FIGS. 11-17 includes the guide 20 in use with the rod insertion system 100. FIG. 18 includes another application with the guide in use with a carriage 110 attached to a single extender 101. The carriage 110 pivots about pivot axis X and guide 20 is attached in a similar manner as described above. The carriage 110 introduces the guide 20 into the patient and aligns the distal end 21 of the guide 20 with the first anchor 90. As described above, the guide 20 may be aligned relative to just the first anchor 90, or may extend through the first anchor 90 and align with a subsequent anchor 90. After the guide 20 is positioned within the patient, the carriage 110 is pivoted to the second orientation removing the inserter 120 from the guide 20. The elongated member 30 may be attached to the inserter 120 as described above, or may be inserted by hand by the surgeon.

Figure 19:
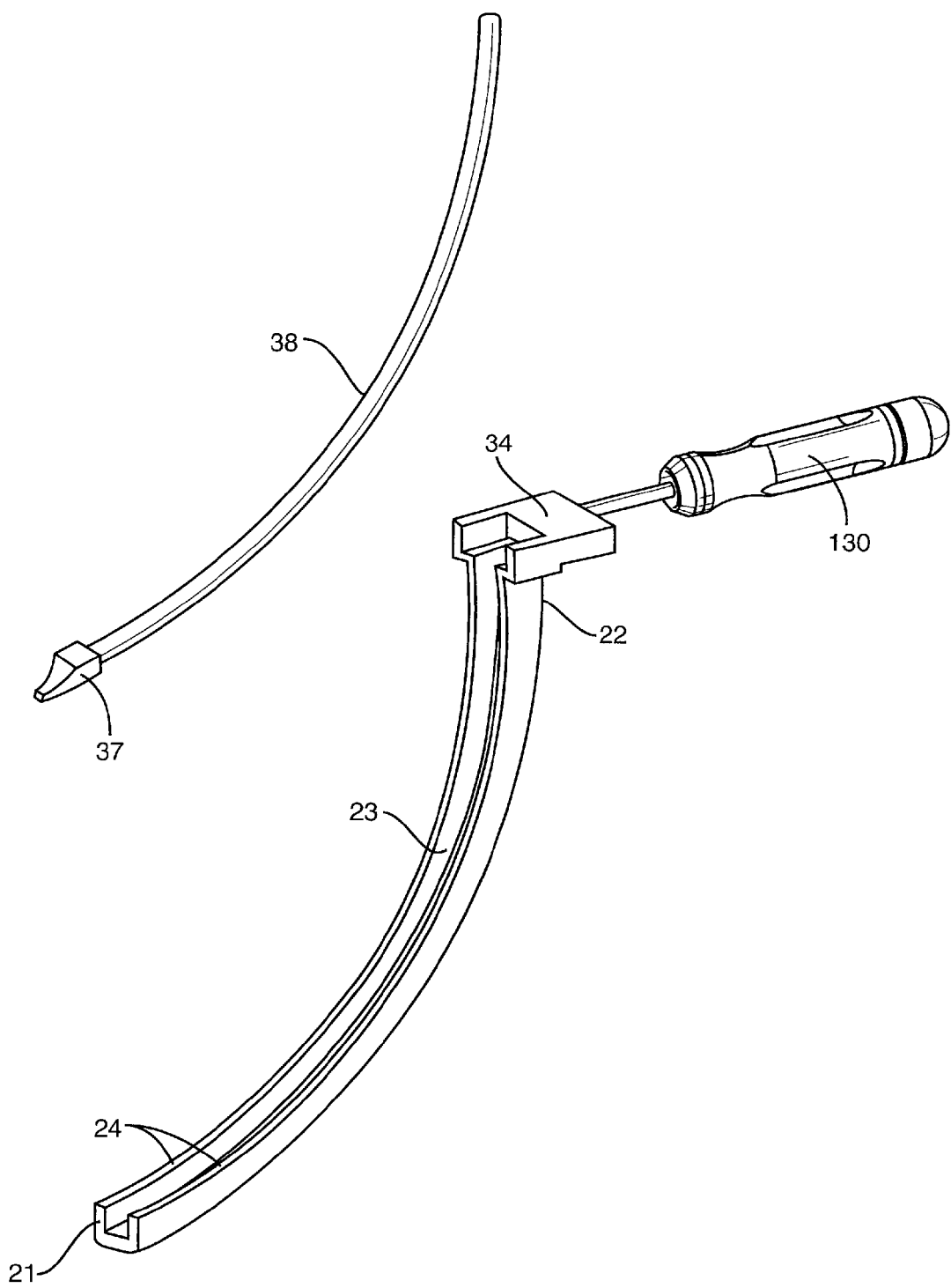
FIG. 19 is a perspective view of a guide and a detached trocar according to one embodiment.

FIG. 19 illustrates another embodiment of a guide 20 for insertion in a freehand method by the surgeon. Guide 20 includes a handle 130 mounted at the proximal end 22 for grasping and manipulating the guide 20 by the surgeon. In one embodiment, a trocar 37 is attached to the distal end 21 to facilitate insertion into the patient. The trocar 37 includes a sharpened tip for insertion through the skin 101 and tissue during positioning within the patient. Trocar 37 may also prevent tissue from entering into the channel 23 as the guide 20 is introduced into the patient. This keeps the channel 23 free for insertion of the elongated member 30. In one embodiment, trocar 37 is a separate member that attaches to the distal end 22. In another embodiment, trocar 37 is attached to an elongated extension 38. The trocar 37 is positioned at the distal end 21 with the extension 38 positioned within the channel 23 and extending outward from the proximal end 22. Once the guide 20 is inserted within the patient, the trocar 37 may be removed through the channel 23 by pulling on the extension 38.

Figure 20:
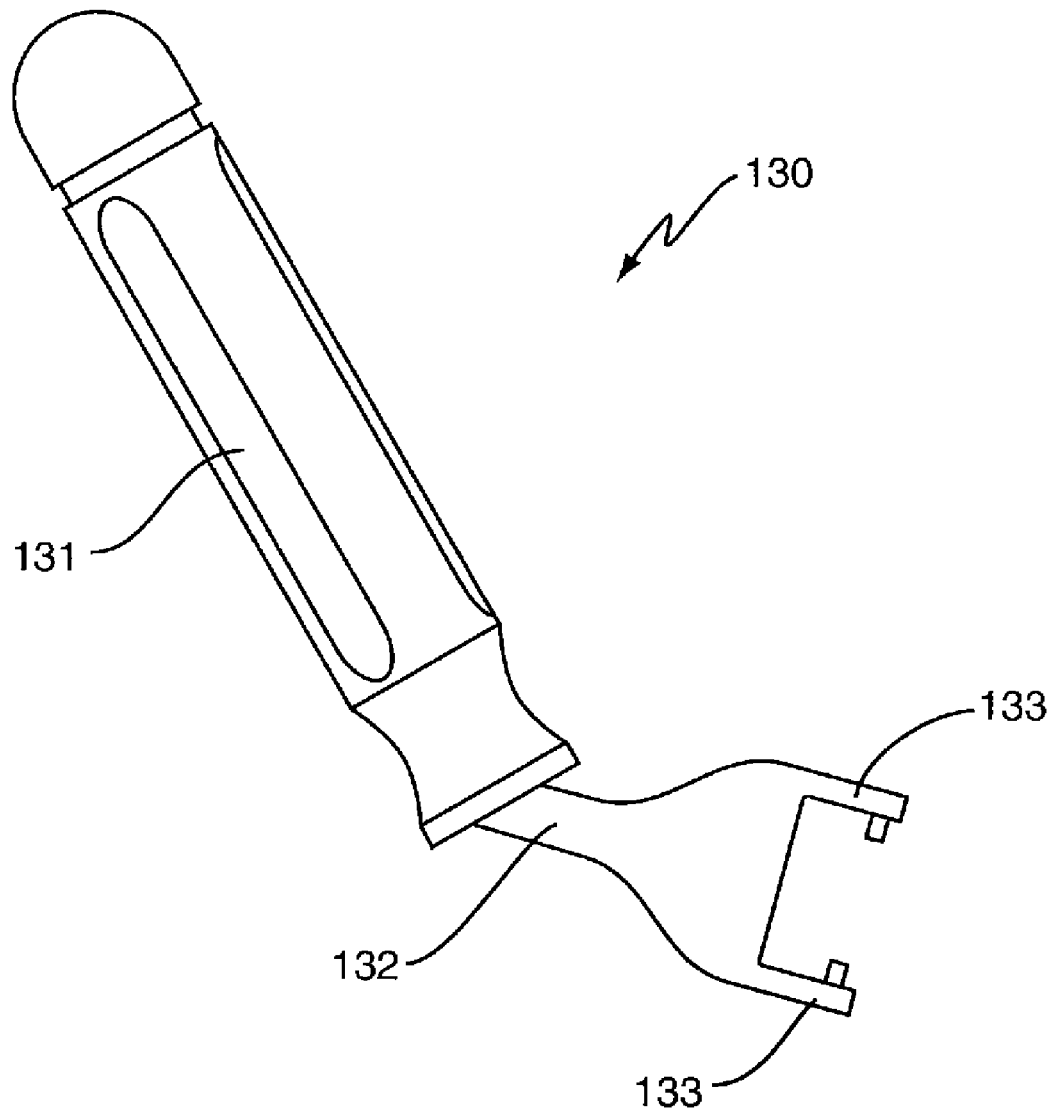
FIG. 20 is a perspective view of a handle according to one embodiment.

In one embodiment, handle 130 is permanently attached to the guide 20. In another embodiment, handle 130 is removably attached to the guide 20. FIG. 20 illustrates a removable handle 130 that includes a grip 131 for grasping by the surgeon and movable jaws 133. Jaws 133 may be adjusted to extend around and grasp the guide 20. In one embodiment, jaws 133 are positioned distally below the flange 34 at the proximal end of the guide 20. This positioning prevents the handle 130 from inadvertently sliding off of the guide 20.

In one embodiment, an arm may extend outward from the guide 20 for attachment to a support member. The arm secures the position of the guide 20 after being inserted into the patient. The arm further allows the guide 20 to remain in position within the patient without being held by the surgeon.

Various means may be used for percutaneously tracking the position of the guide 20 and/or elongated member 30 during the various insertion applications. Examples include electromagnetic tracking, fluoroscopy and specifically the FluroNav virtual fluoroscopy system, and computed tomography (CT) scanning. In one embodiment, the distal end 21 of the guide 20 is constructed of a material that is transparent to the percutaneous tracking methods to allow the surgeon to observe the positioning of the elongated member 30 into one or more of the anchors 90. The guide 20 may be constructed of a variety of materials including stainless steel, ceramics, PEEK, Nitinol, and polymer materials.

In one embodiment, the guide 20 is positioned on the inserter 120 with the distal ends of each being substantially aligned. In another embodiment, the distal end of the guide 20 extends beyond the distal tip 122 of the inserter 120. In yet another embodiment, the distal end of the guide 20 is positioned inward from the distal tip 122 of the inserter 120.

The elongated member 30 may include a variety of different constructions. Examples include but are not limited to a balloon, tether, jointed rod, and flexible rod.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A device to insert an elongated member into a patient during a surgical procedure, the device comprising:
    an elongated substantially curved guide including a distal end that is placed within the patient and a proximal end that is positioned outside of the patient, the guide including opposing sidewalls and an outer wall that extends between the opposing sidewalls that form a channel sized to receive and partially extend around the elongated member;
    wherein the channel is open along an inner side of the guide opposite from the outer wall and between the sidewalls substantially between the distal end and the proximal end,
    wherein the guide is constructed from first and second sections that are relatively movable to adjust a width of the channel measured between the sidewalls, and
    wherein the first and second sections include opposing tapered sections that connect together to form the outer wall, wherein the first section includes a greater width at the distal end of the guide and the second section includes a greater width at the proximal end of the guide.

2. The device of claim 1 wherein the guide includes a substantially straight section.

3. The device of claim 1, further comprising at least one extension that extends outward from one of the sidewalls and across the channel.

4. A device to insert an elongated member into a patient during a surgical procedure, the device comprising:
    an insertion device comprising at least one anchor extension and a carriage pivotally attached to the anchor extension, the carriage including an inserter with a curved shape that terminates at a tip; and
    a guide including opposing sidewalls and a back wall that form a channel with an open side opposite from the back wall that is sized to extend around and attach with a section of the carriage, the guide including an elongated shape with a distal end and a proximal end, the open side facing towards the carriage and extending along a substantial length of the guide between the distal and proximal ends;
    the carriage pivotable between a first orientation with the inserter and the guide positioned exterior to the patient and a second orientation with the inserter and the guide inserted into the patient;
    the guide sized to be removable from the inserter and remaining within the patient when the carriage is pivoted from the second orientation to the first orientation, the guide being positioned with the distal end remaining within the patient and the proximal end positioned outside of the patient, and
    a locking mechanism to lock the guide to the inserter.

5. The device of claim 4, further comprising an extension that extends from the sidewalls and across the open side of the channel.

6. The device of claim 4, wherein the channel includes a tapered width that reduces from the proximal end towards the distal end.

7. The device of claim 4, wherein the distal end of the guide includes a pair of opposing fingers separated by an opening that is aligned with the channel.

8. The device of claim 4, wherein the guide is constructed of first and second sections that are operatively connected together, the first and second sections being relatively movable to adjust a width of the channel.

9. The device of claim 8, wherein the first section includes a tab and the second section includes a receptacle, the tab being sized to adjustably fit within the receptacle.

10. The device of claim 4, wherein the guide is curved along a substantial section of the length.

11. The device of claim 4, wherein the guide includes a substantial straight section and a curved section.

12. The device of claim 4, further including a handle that is attached to an exterior surface of the guide.

* * * * *